US00PP30513P3

(12) United States Plant Patent
Clark et al.

(10) Patent No.: US PP30,513 P3
(45) Date of Patent: May 21, 2019

(54) GRAPE PLANT NAMED 'ENCHANTMENT'

(50) Latin Name: ***Vitis* L. hybrid**
Varietal Denomination: Enchantment

(71) Applicant: THE BOARD OF TRUSTEES OF THE UNIVERSITY OF ARKANSAS, Little Rock, AR (US)

(72) Inventors: John Reuben Clark, Fayetteville, AR (US); James N. Moore, Arlington, TX (US); Justin R. Morris, Springdale, AR (US); Renee Threlfall, Springdale, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 15/731,615

(22) Filed: Jul. 7, 2017

(65) Prior Publication Data

US 2019/0014700 P1 Jan. 10, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
See application file for complete search history.

(56) References Cited

U.S. PATENT DOCUMENTS

| | | | |
|---|---|---|---|
| PP13,309 | P2 | 12/2002 | Clark et al. |
| PP25,152 | P3 | 12/2014 | Clark et al. |
| PP25,696 | P3 | 7/2015 | Clark et al. |
| PP25,697 | P3 | 7/2015 | Clark et al. |
| PP25,726 | P3 | 7/2015 | Clark et al. |
| PP25,746 | P3 | 7/2015 | Clark et al. |

OTHER PUBLICATIONS

Clark, Moore, Morris and Threlfall, 'Opportunity' and 'Enchantment' Wine Grapes for the Mid-South of the United States, HortScience Aug. 2018 53:1208-1211.

Hightower, Grape, breeder travel the long road to a good Arkansas wine grape, University of Arkansas Cooperative Extension Service News, Nov. 10, 2016 available at https://www.uaex.edu/media-resources/news/november2016/11-10-2016-Ark-Long-Grape-Journey.aspx.

MC Kee, New Wine Grape Varieties for the Mid-South University of Arkansas names Opportunity, a white grape, and Enchantment, a red grape, Sep. 30, 2016, Wines & Vines available at https://www.winesandvines.com/news/article/175263/New-Wine-Grape-Varieties-for-the-Mid-South.

*Primary Examiner* — Keith O. Robinson
(74) *Attorney, Agent, or Firm* — Andrus Intellectual Property Law, LLP

(57) ABSTRACT

Description and specifications of a new and distinct wine grape cultivar which originated from a hand-pollinated cross of Ark. 1628 (non-patented, non-released breeding genotype; female parent) x Ark. 1481 (non-patented, non-released breeding genotype; male parent). This new wine grape cultivar can be distinguished by its quality juice attributes for wine production with hardy and productive grapevines adapted Arkansas and the Mid-South of the United States.

4 Drawing Sheets

Latin name: *Vitis* L. hybrid.
Varietal denomination: 'Enchantment'.

BACKGROUND

The new and distinct cultivar of red wine grape named 'Enchantment' is described herein. The new cultivar originated from a hand-pollinated cross of 'Ark. 1628' (female parent) and 'Ark. 1481' (male parent) made in 1990. The seedlings fruited in the summer of 1993 in a vineyard near Clarksville, Ark. and one was selected for its potential as a red wine grape for utilization in Arkansas and the Mid-South of the United States. The fruit grows in medium-sized clusters on hardy and consistently productive plants and produces deep-colored juice ideal for wine production.

SUMMARY OF THE INVENTION

The new and distinct cultivar of grapevine originated from a hand-pollinated cross of 'Ark. 1628' (non-patented, non-released breeding genotype; female parent) x 'Ark. 1481' (non-patented, non-released breeding genotype; male parent) made in 1990 near Clarksville, Ark. The seeds resulting from this controlled hybridization were germinated in a greenhouse during the winter of 1990-91. Resulting seedlings were planted in the spring of 1991 in a vineyard near Clarksville, Ark. The seedlings fruited in the summer of 1993 and one seedling, designated Arkansas Selection 2467, was selected for good productivity and its potential for red wine production along with good adaptation to Arkansas and Mid-South of the United States.

During late 1993 and early 1994, the original plant selection was propagated asexually at the above-noted location, by rooting hardwood cuttings and a test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained.

All vines planted from hardwood cutting propagation fruited in the third season of growth in the vineyard after planting.

Vines of the new cultivar have medium-high, but not excessive, vigor, with semi-procumbent growth habit intermediate between *V. vinifera* and *V. labrusca* hybrids. It has produced well as own-rooted plants in all testing and has not been evaluated on any rootstocks. Adaptation to the Arkansas test site is very good as winter injury and heat damage were not observed.

The health of the new cultivar is good. The new cultivar is moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopora viticola* Berl. & Tomi.), and anthrancnose (*Elsinoe ampelina* (d. By.) Sher), but susceptible to black rot (*Guignardia bidwellii* (Ell.) V. & R.). It is also susceptible to Pierce's disease (*Xylella fastidiosa*). Fungal diseases can be controlled by the use of available fungicides.

The new cultivar average harvest date is 22 August. Yield averages 10.1 kg/vine with average cluster weight of 178.3 g. Medium-sized clusters are compact, but not excessively tight. The berries are small (ca. 1.5 g). 'Enchantment' is a teinturier grape with color in the flesh and juice. Fruit cracking was not observed during evaluation in summer rainfall near maturity.

The flavor attributes for the new cultivar are reflective of commercial standards for quality juice and wine. Wine quality of the new cultivar is comparable to 'Cynthiana' (not-patented). Soluble solids and titratable acidity concentration of the juice at fruit maturity averages 18.9% and 0.8%, respectively. Juice pH average is 3.4. The crush juice yield is 4.9 kg of grapes for 3.8 L of juice. The primary anthocyanin pigment present in the wine is malvidin-3-glucoside. The wine from 'Enchantment' has a deep, dark red color and a "cherry-like" aroma with flavors similar to 'Petit Syrah' (not-patented).

The new cultivar has been named 'Enchantment'.

BRIEF DESCRIPTION OF THE PHOTOGRAPHS

The accompanying photographs show typical specimens from 22 year-old vines of the new cultivar in color as nearly true as it is reasonably possible to make in a color illustration of this character.

DETAILED DESCRIPTION OF THE NEW CULTIVAR

Figure 1:
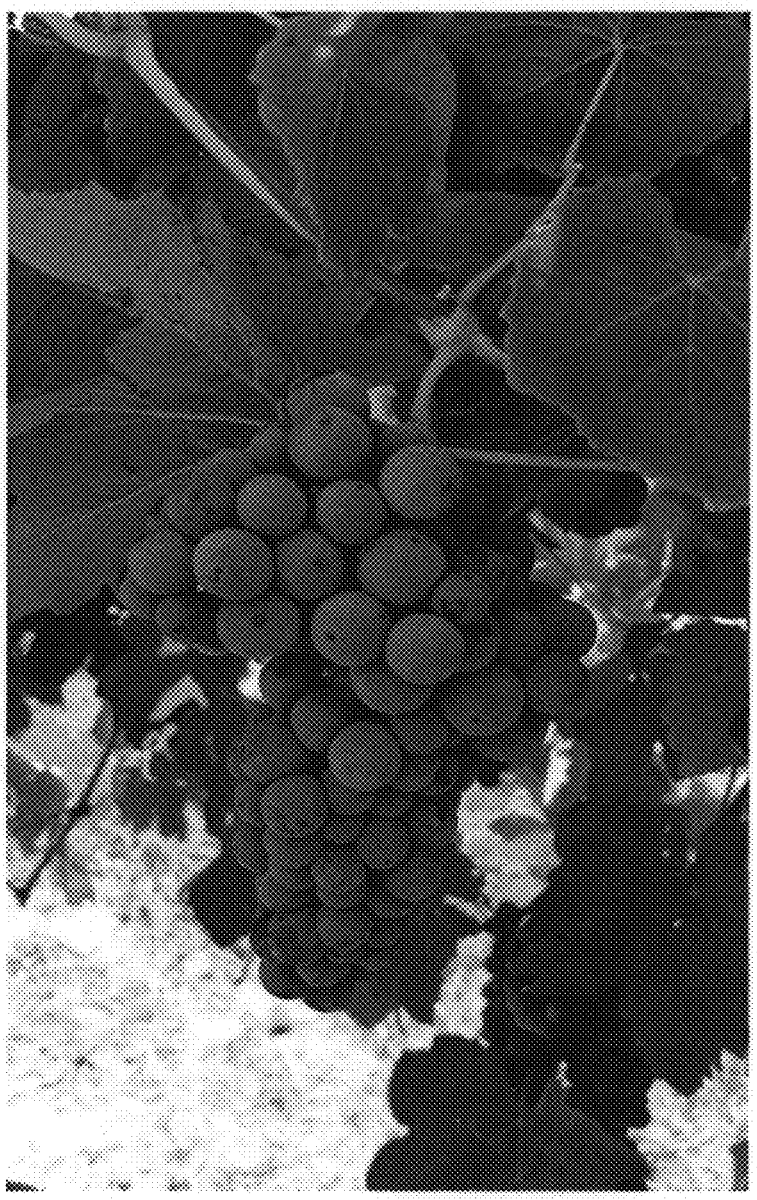
FIG. 1 is a photograph showing typical cluster of healthy fruit, near Clarksville, Ark.
Figure 2:
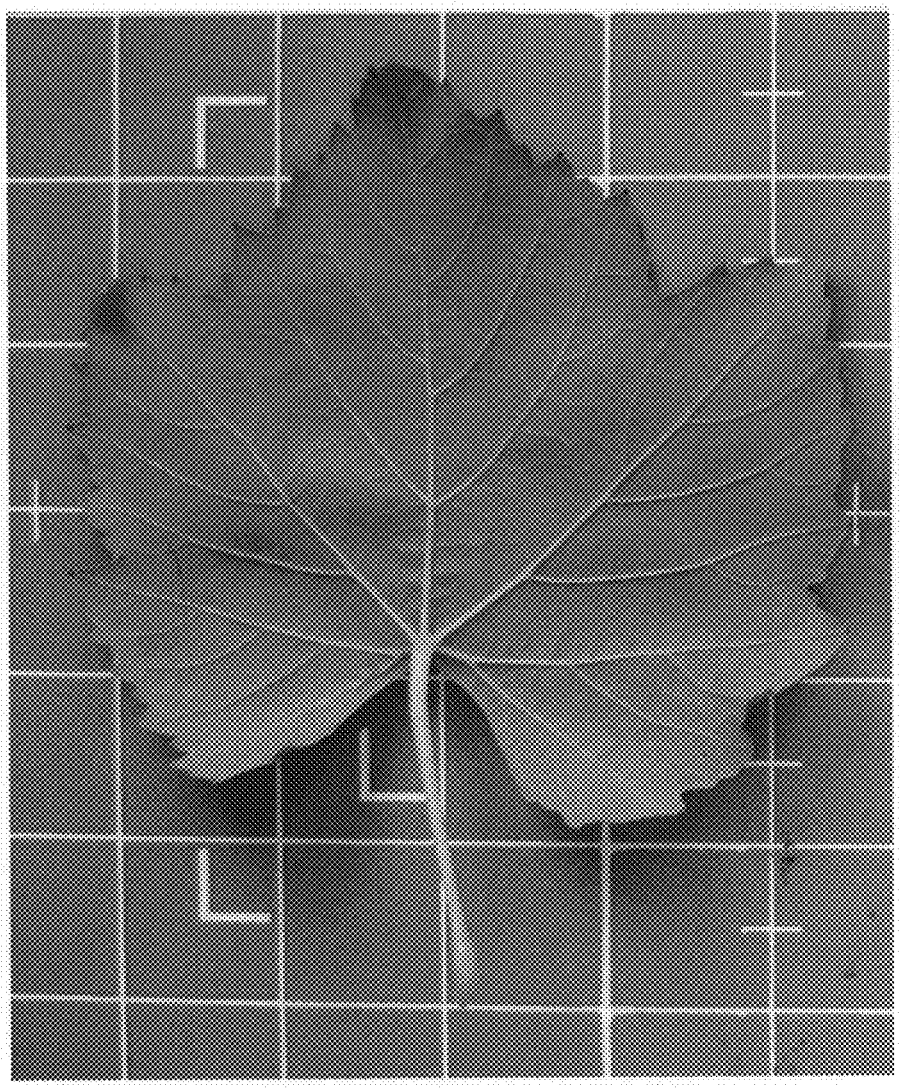
FIG. 2 is a photograph showing the leaf abaxial view, near Clarksville, Ark.
Figure 3:
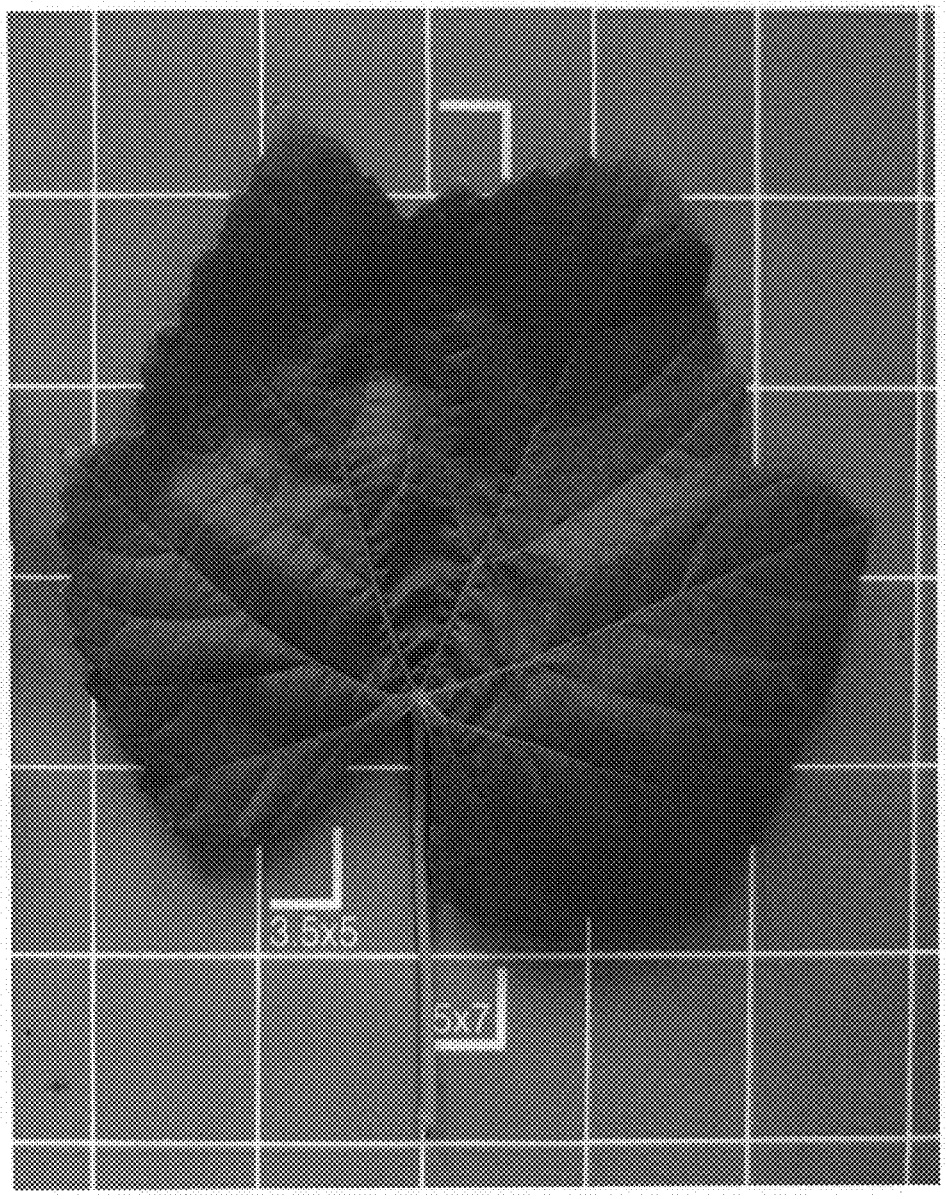
FIG. 3 is a photograph showing the leaf adaxial view, near Clarksville, Ark.
Figure 4:
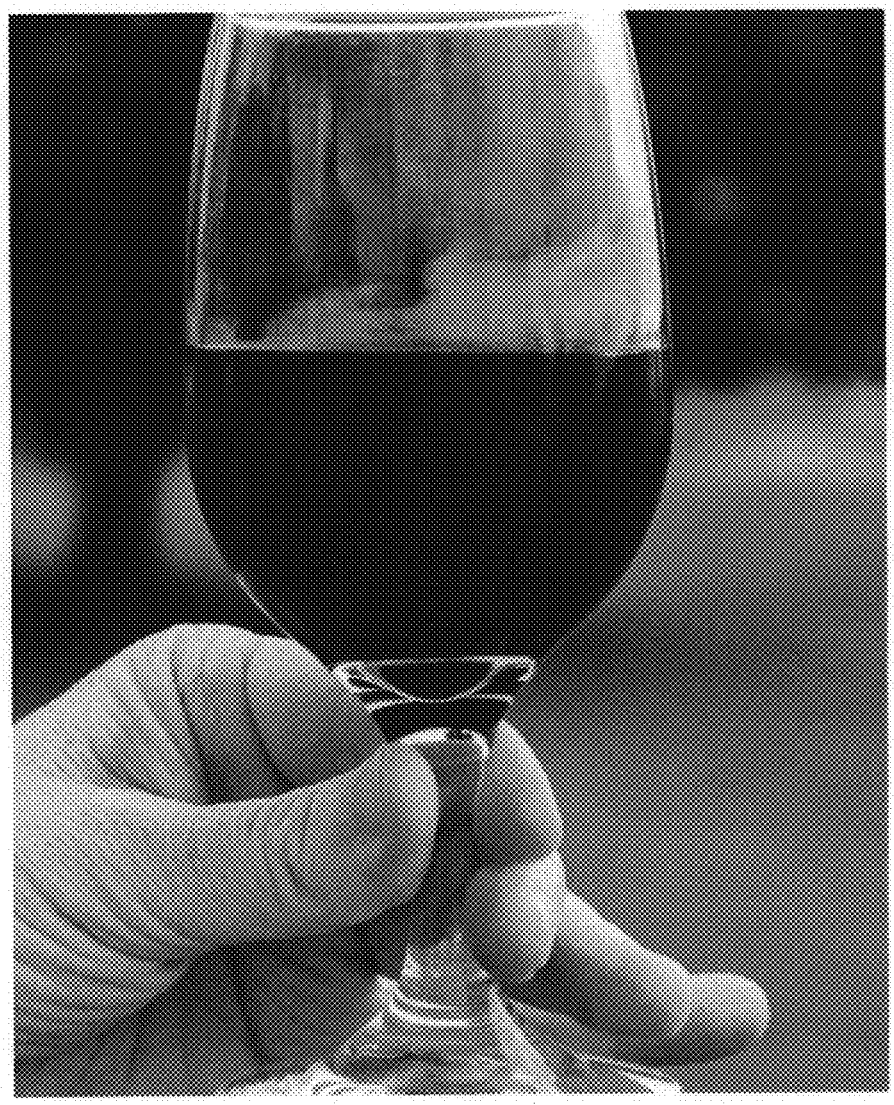
FIG. 4 is a photograph of the wine.

'Enchantment' differs from its female parent Ark. 1628 in that 'Enchantment' has larger clusters, is more winter hardy, and is more consistent in producing adequate yield. 'Enchantment' differs from it male parent Ark.1481 as it is more winter hardy, more disease resistant, and is more productive.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. Vines were fertilized annually in spring with Nitrogen or complete fertilizers. No shoot or leaf thinning practices were conducted on the vines. The data collection was from vines that were 22 years old.

Vine:

*Size.*—Medium. Evaluation vines grown on a 5 ft high, single-wire trellis, bilateral cordon training system spaced 8 ft between vines occupy vine space fully.

*Growth vigor.*—Medium vigor.

*Density of foliage.*—Thick.

*Productivity.*—Moderately productive. Yields average 22 lb/vine (10.1 kg/vine). The comparison wine grape cultivar 'Chambourcin' had a yield of 22 lb/vine.

*Rootstock.*—None; vines tested were own-rooted vines.

*Cold hardiness.*—Hardy to −17° C. (1° F.); potentially more hardy as this was the coldest temperature experienced at the test site.

Shoots (current-season canes):

*Color of shoots (current-season canes).*—Sun exposed side: greyed-orange group 175-B; shaded side: yellow-green group 146-C; anthocyanin minimally present on shoot sides exposed to direct sunlight.

*Shoot attitude.*—semi-procumbent.

Canes (mature, dormant):

*Color of mature, dormant cane.*—Base: brown group 200-D; midpoint: greyed-orange group 165-B; terminal: greyed-orange group 165-B; anthocyanin present on mature canes at base on all sides and only on sun exposed sides of midpoint and terminal portions of canes.

*Texture of mature, dormant canes.*—Smooth.

*Length of mature, dormant canes.*—Average 1.1 m with range of 0.8 to 1.5 m.

*Diameter of mature, dormant cane.*—Base: 1.0 cm; midpoint: 0.8 cm; terminal: 0.6 cm.

*Internode length of mature, dormant canes.*—Base: 5.2 cm; midpoint: 6.0 cm; terminal: 4.4 cm.

*Lenticels.*—Not present on mature canes. Cane maturity in the fall extends to most of the cane length but not complete to distal ends.

Trunk:

*Diameter at 30 cm above soil level.*—5.1 cm.

*Shape.*—Round.

*Trunk straps.*—Present.

*Surface texture.*—Rough.

*Color.*—Inner bark color: brown group 200-C; outer bark color: greyed green 197-A.

Foliage:

*Leaves.*—

*Arrangement of mature leaves.*—Simple and alternate.

*Shape of mature leaves.*—Pentagonal.

*Number of lobes on mature leaves.*—4-5.

*Petiole sinus of mature leaves.*—*Open, triangular.*

*Venation of mature leaves.*—Palmate.

*Margin of mature leaves.*—Serrated with teeth shape of mature leaves rounded and medium in size; teeth height: 3.4 mm; teeth width: 5.6 mm.

*Surface texture of mature leaves.*—Abaxial side: smooth; adaxial side: smooth.

*Dimensions of mature leaves.*—Length: 11.4 cm; width: 15.1 cm; thickness: 0.02 cm.

*Pubescence on mature leaves.*—Abaxial side: none; adaxial side: none.

*Color of mature leaves.*—Base abaxial: green group 141-A; base adaxial: yellow-green group 146-B; midpoint abaxial: green group 141-A; midpoint adaxial: yellow-green group 146-B; terminal abaxial: green group 141-A; terminal adaxial: yellow-green group 146-B.

*Color of veins on mature leaves.*—Abaxial surface: yellow-green group 141-D; adaxial surface: yellow-green group 144-A; no anthocyanin on upper or lower surfaces of leaves or on leaf veins.

*Autumn coloration of mature leaves.*—Abaxial surface: greyed-orange group 176-B; adaxial surface: grayed-purple group 183-A.

*Leaf pubescence on young leaves.*—Abaxial side: low; adaxial side: low to none.

*Color of young leaves.*—Base abaxial: yellow-green group 144-B; base adaxial: yellow-green group 144-B; midpoint abaxial: yellow-green group 144-B; midpoint adaxial: yellow-green group 144-B; terminal abaxial: yellow-green group 144-B; terminal adaxial: yellow-green group 144-B; anthocyanin minimally present on tips of young leaves.

*Vein color of young leaves.*—Abaxial side: yellow-green group 144-B; adaxial side: yellow-green group 144-B.

Petioles:

*Color of mature petioles.*—Yellow-green group 146-D; anthocyanin minimally present on mature petioles exposed to sun.

*Dimensions of mature petioles.*—Length: 8.3 cm; diameter: 0.3 cm.

*Shape of mature petioles.*—Round.

*Pubescence on mature petioles.*—None.

*Color of young petioles.*—Yellow-green group 144-B.

Tendrils: Found on the 6th node.

*Orientation.*—Intermittent.

*Dimensions.*—Length: 10.1 cm; diameter: 0.2 cm.

*Texture.*—Smooth.

*Color of mature tendril.*—Grey group 201-A. Tendril forked and mostly curled.

Buds:

*Number of buds on current, single-season cane.*—14.

*Dimensions of dormant buds.*—Length: 0.5 cm; width of dormant buds: 0.3 cm.

*Shape of dormant buds.*—Triangular.

*Color of dormant buds.*—Greyed-orange group 173-A.

*Texture of dormant buds.*—Smooth; bumpy where scales meet.

*Bud break.*—28 March.

Disease resistance: Moderately resistant to powdery mildew, downy mildew, and anthracnose, and susceptible to black rot. Susceptible to Pierce's disease. Other disease susceptibilities not known.

Flower:

*Fragrance.*—Similar to *Vitis vinifera* vines.

*Sex.*—Hermaphrodite.

*Bloom dates.*—First bloom: 9 May; full bloom: 15 May.

*Flowers per cluster.*—519.

*Inflorescence dimensions.*—Length: 8.6 cm; diameter: 4.1 cm.

*Flower dimensions.*—Length: 0.4 cm; diameter: 0.7 cm.

*Flower longevity.*—Moderate.

*Flower shape.*—Roundish.

Stamens:

*Number.*—4.

*Color of filament.*—Yellow-orange group 15-A.

Pistil:

*Number.*—1.

*Length.*—0.2 cm.

*Color.*—Yellow-green group 144-A.

Pollen:

*Color.*—Yellow-orange group 15-A.

*Amount.*—Moderately abundant.

Petal:

*Number.*—6 fused petals, form calyptra (flower cap).

*Color.*—Yellow-green group 144-A.

Sepal: None.

Pedicle:

*Dimensions.*—Length: 0.5 cm; diameter: 0.1 cm.

*Color.*—Red group 46-A.

Fruit:

*Maturity.*—22 August.

*Berry shape and cross section.*—Round.

*Berry color.*—Skin: black group 202-A.

*Berry flesh color.*—Very strong; greyed-purple group 187-C.

*Berry dimensions.*—Diameter at equator: 1.4 cm; diameter at base: 1.0 cm; diameter at apex: 1.0 cm; length: 1.3 cm.

*Berry weight.*—1.5 g. The comparison wine grape cultivar 'Chambourcin' had an average berry weight of 1.4 g/berry.

*Berry texture.*—Smooth.

*Firmness.*—Slightly firm; rupture force to penetrate berry 11.9 N.

*Skin thickness.*—0.04 cm.

*Tenacity.*—High.

*Seeds.*—Yes. 2-3 developed/complete.

*Brush length.*—0.2 cm.

*Juiciness.*—Very juicy.

*Attachment.*—Strong, very good, difficult to remove grape from pedicel at maturity.

*Aroma.*—None to mild. Herbaceous, slight blackberry.

*Flavor.*—Blackberry, mulberry, dark cherry, bell pepper.

Juice:

*Color.*—Red group 53-B.

*Soluble solids.*—18.9%.

*Titratable acidity.*—0.8%.

*ph.*—3.4.

Seed:

*Number per berry.*—2.

*Seed dimensions.*—Length: 0.6 cm; width: 0.4 cm.

*Weight.*—0.04 g.

*Color.*—Greyed-orange group 166-A.

*Shape.*—Obovate.

Cluster:

*Weight.*—178.3 g.

*Cluster dimensions.*—Length: 16.8 cm; width: 10.9 cm.

*Berries per cluster.*—154. The comparison wine grape cultivar 'Chambourcin' had an average of 79 berries per cluster.

*Cluster per vine.*—150. The comparison wine grape cultivar 'Chambourcin' had an average 80 clusters/vine.

*Cluster density.*—Medium.

*Clusters per shoot.*—2.4.

*Peduncle length.*—3.1 cm.

Wine quality:

*Flavor.*—Earthy, mildly vegetative; black pepper, anise.

*Aroma.*—Fresh, "cherry-like"; mildly vegetative for non-aged wine.

*Color.*—Deep, dark red-purple.

*Finish.*—medium length, non-lingering.

*Overall quality.*—Comparable to established regional cultivars such as 'Chambourcin' or 'Cynthiana'.

Use: Processing for red wine with improved vines particularly adapted for Arkansas and the Mid-South of the United States.

The cultivar: The most distinctive features of this cultivar are vines with consistent productivity, teinturier grapes with juice quality for red wine production, and plants with adaptation to Arkansas and the Mid-South of the United States.

We claim:

1. A new and distinct cultivar of grape plant named 'Enchantment', substantially as illustrated and described.

* * * * *